United States Patent

Tsujino

[11] Patent Number: 5,914,133
[45] Date of Patent: Jun. 22, 1999

[54] WASHING AGENTS

[75] Inventor: Rieko Tsujino, Kanagawa-ken, Japan

[73] Assignee: Asahi Kogaku Kogyo Kabushiki Kaisha, Tokyo, Japan

[21] Appl. No.: 08/825,347

[22] Filed: Mar. 28, 1997

[30] Foreign Application Priority Data

Apr. 1, 1996 [JP] Japan ..................................... 8-079114
Oct. 18, 1996 [JP] Japan ..................................... 8-276308

[51] Int. Cl.$^6$ ...................................................... A61K 9/14
[52] U.S. Cl. ........................... 424/489; 424/401; 424/59; 424/76.2; 424/76.25
[58] Field of Search ..................................... 424/489, 401, 424/59; 252/91, 102, 8.8

[56] References Cited

U.S. PATENT DOCUMENTS

| | | | |
|---|---|---|---|
| 3,975,280 | 8/1976 | Hachmann et al. | 252/102 |
| 4,664,817 | 5/1987 | Wixon | 252/8.8 |
| 4,666,740 | 5/1987 | Wixon | 427/214 |
| 5,122,418 | 6/1992 | Nakane et al. | 424/401 |
| 5,182,103 | 1/1993 | Nakane et al. | |
| 5,310,548 | 5/1994 | Tsuru et al. | |
| 5,540,995 | 7/1996 | Kitano et al. | |
| 5,545,240 | 8/1996 | Tsuru et al. | |
| 5,567,231 | 10/1996 | Yokoo et al. | |

FOREIGN PATENT DOCUMENTS

| | | |
|---|---|---|
| 62-195317 | 8/1987 | Japan . |
| 63-96110 | 4/1988 | Japan . |
| 1186814 | 7/1989 | Japan . |

*Primary Examiner*—Thurman K. Page
*Assistant Examiner*—William E. Benston, Jr.
*Attorney, Agent, or Firm*—Greenblum & Bernstein P.L.C.

[57] ABSTRACT

A washing agent which comprises spherical particles having an average particle diameter in the range of about 2 to 40 microns, at least a surface portion of which particles comprises or consists of, or consists essentially or substantially of a calcium phosphate compound having a Ca/P ratio in the range of about 1.0 to 2.0, and spherical particles having an average particle diameter in the range of about 80 to 200 microns, at least a surface portion of which particles comprises or consists of, or consists essentially or substantially of a calcium phosphate compound having a Ca/P ratio in the range of about 1.0 to 2.0. The washing agent, when used in cleaning of the feet and elbows, can remove a wide variety of bacteria, thereby making the feet and elbows clean, in addition to removing the aged and deteriorated cuticles.

20 Claims, No Drawings

WASHING AGENTS

BACKGROUND OF THE INVENTION

1. Field of the Invention

The present invention relates to a washing agent, more specifically, a liquid, creamy, gel-like or solid washing agent having excellent functions in the removal of both the aged cuticles and bacteria.

2. Description of the Related Art

Among the constituent parts of the human body, the feet are generally contained in a closed space such as shoes or other footwear for a substantial period of time in the life environment, and accordingly they suffer from perspiration and secretion. As a result of the perspiration and secretion, parts of or sites on the feet may experience accelerated growth of a variety of bacteria and others and cause the generation of offensive odor, and the feet are in a filthy condition. To avoid these problems, the feet have to be cleaned with a washing agent. However, at present, a satisfactory washing agent designed for foot cleaning is not available. This is because the users have little or no concept of cleaning their feet only with exclusive washing agents, and they used to wash their feet along with other body parts with conventional washing agents designed for washing the whole body such as body shampoos and soaps or bath soaps.

However, the above-mentioned conventional washing agents do not solve the problems in foot cleaning, because the feet parts, particularly a bottom portion thereof, have a cuticle layer thicker than that of other body parts, and accordingly the conventional washing agents can effectively clean only the surface of the cuticle layer. Because of such a limited effective cleaning area, the resulting bacteria removal and bactericidal effects are also limited to only the surface of the cuticle layer, and the resulting deodorizing effect is also unsatisfactory.

SUMMARY OF THE INVENTION

The object of the present invention is to provide a washing agent which, when applied to feet, elbows and similar parts of the human body, can remove the aged and deteriorated cuticles and at the same time can remove a variety of miscellaneous bacteria, thereby making the washed parts clean.

According to the present invention, the object can be accomplished by using two types of spherical particles of calcium phosphate compound having different average particle diameters, in which the calcium phosphate particles having a relatively large particle diameter can principally fill the role of removing the cuticles and the calcium phosphate particles having a relatively small particle diameter can principally act as a means of adsorption removing the bacteria, dirt and the like.

Namely, the washing agent of the present invention is characterized by comprising spherical particles having an average particle diameter of about 2 to 40 microns, at least a surface portion of which particles comprises or consists of, or consists essentially or substantially of a calcium phoshate compound having a Ca/P ratio in the range of about 1.0 to 2.0, and spherical particles having an average particle diameter of about 80 to 200 microns, at least a surface portion of which particles comprises or consists of, or consists essentially or substantially of a calcium phosphate compound having a Ca/P ratio in the range of about 1.0 to 2.0.

Since it has a high polishing function capable of removing the cuticle layer, along with a high washing-off function of the dirt, bacteria and the like, the washing agent of the present invention is useful in both the cleaning of the elbow portions and the bottom portions of the feet and the removal of the cuticles from said portions. Further, excessive polishing of the cuticle layer can be avoided, because the particles used as one essential component of the present washing agent, at least a surface portion of said particles being made of calcium phosphate compound, are each in the form of a sphere. Furthermore, because of its high adsorptive removal function to a variety of miscellaneous bacteria, when it is applied to the bottom portions of the feet, the present washing agent can remove the bacteria from a whole region of said portions and particularly it can adsorb and remove the trichophytons, along with removal of the grown and thickened cuticle layer. In addition to the cleaning effect of the feet portions, the present washing agent can also provide a deodorizing effect.

The present disclosure relates to subject matter contained in Japanese Patent Application No. 08-79114 (filed on Apr. 1, 1996) and No. 08-276308 (filed on Oct. 18, 1996) which are expressly incorporated herein by reference in their entireties.

PREFERRED EMBODIMENTS OF THE PRESENT INVENTION

Spherical particles are understood as including particles which are not in perfect spherical form. It is accordingly understood that reference herein to spherical particles includes particles which are generally spherical, or substantially spherical, or essentially spherical.

The washing agent according to the present invention, as described above, contains two types of spherical particles having different particle diameters, at least a surface portion of which particles comprises or consists of, or consists essentially or substantially of a calcium phosphate compound having a Ca/P ratio in the range of about 1.0 to 2.0. One type of the spherical particles is the spherical particles having an average particle diameter in the range of about 2 to 40 microns (hereinafter also referred to as "spherical particles of smaller particle diameter"), and another one is the spherical particles having an average particle diameter in the range of about 80 to 200 microns (hereinafter also referred to as "spherical particles of larger particle diameter").

The spherical particles of larger particle diameter have a polishing function, and accordingly they can effectively remove the old and deteriorated cuticles. From the viewpoint of obtaining the desired polishing function, the spherical particles should preferably have an average particle diameter in the range of about 80 to 200 microns, more preferably in the range of about 85 to 130 microns.

Sole use of the spherical particles of larger particle diameter is likely to cause a varied adsorption of the bacteria and dirt on the particle surface. To avoid this undesirable liability, in the washing agent of the present invention, the spherical particles of smaller particle diameter are incorporated, in addition to the spherical particles of larger particle diameter, in order to attain a highly increased adsorptivity. The spherical particles of smaller particle diameter should preferably have an average particle diameter in the range of about 2 to 40 microns. The particle diameter of less than about 2 microns has a tendency of causing introduction of the particles into pores of the skin and clogging the pores. The particle diameter above about 40 microns has a tendency of causing an uneven contact of the particles with the bacteria and dirt. More preferably, the spherical particles of smaller particle diameter should have an average particle diameter in the range of about 10 to 35 microns.

In the washing agent of the present invention, although it can be varied depending upon the specific form of the washing agent such as liquid, emulsified cream, gel or solid, a ratio by weight between the spherical particles of smaller particle diameter and the spherical particles of larger particle diameter is preferably in the range of about 50:50 to 99.9:0.1.

The spherical particles, at least a surface portion of which particles comprises or consists of, or consists essentially or substantially of a calcium phosphate compound having a Ca/P ratio in the range of about 1.0 to 2.0, are preferably contained in the washing agent in a total amount of about 0.01 to 10% by weight. The total amount of less than about 0.01% by weight means that a satisfactory washing effect can not be expected because of the reduced probability of contact between the spherical particles and the skin. Similarly, even if said total amount increases beyond about 10% by weight, a further increase of the washing effect can not be expected, and also the touch or feeling during use of the washing agent is deteriorated. More preferably, said total amount of the spherical particles is about 0.1 to 5% by weight.

The spherical particles, at least a surface portion of which particles comprises or consists of, or consists essentially or substantially of a calcium phosphate compound having a Ca/P ratio in the range of about 1.0 to 2.0, may be either spherical particles, a whole body of which particles are constituted from a calcium phosphate compound having a Ca/P ratio in the range of about 1.0 to 2.0, or spherical inorganic or organic particles being coated on a surface thereof with a calcium phosphate compound having a Ca/P ratio in the range of about 1.0 to 2.0, and these spherical particles can be produced by using any conventional methods.

In the practice of the present invention, the calcium phosphate compound having a Ca/P ratio in the range of about 1.0 to 2.0 used herein is not restricted, and such calcium phosphate compound is preferably one or more members selected from the group consisting of hydroxyapatite, fluorapatite, tri-calcium phosphate, tetrabasic calcium phosphate and others, i.e., $Ca_{10}(PO_4)_6(OH)_2$, $Ca_{10}(PO_4)_6F_2$, $Ca_{10}(PO_4)_6Cl_2$, $Ca_3(PO_4)_2$, $Ca_2P_2O_7$, $Ca_4O(PO_4)_2$, $CaHPO_4$ and others. Among these calcium phosphate compounds, the most preferred one is a calcium phosphate compound which contains hydroxyapatite as a principal component thereof.

For example, the spherical particles comprising, wholly consisting of, or consisting essentially or substantially of the calcium phosphate compound can be produced by using any conventional granulation methods, such as by spray-drying a slurry—preferably, a slurry comprising water as the liquid medium—of the calcium phosphate compound and then granulating the dried product to obtain the intended particles of the calcium phosphate compound. Of course, other granulation methods may be used in the production of the spherical particles, if desired. Preferably, sieve and other separation means may be used to obtain the calcium phosphate particles having the predetermined range of the particle diameter depending on the intended use of the particles.

Further, the particles of the calcium phosphate compound used may be either dense particles or porous particles, and they are preferably porous particles which comprise agglomerated primary particles having a specific surface area of not less than about 10 $m^2/g$ and pore size in the range of about 500 to 1000 angstroms. The particles having a specific surface area of less than about 10 $m^2/g$ should be avoided, because such specific surface areas do not ensure satisfactory adsorption. In addition, in order to assist in an effective introduction of the bacteria, dirt and other substances into pores of the particles as a result of the adsorption of said substances, it is preferred that the porous particles contain pores having the above-defined pore size in the range of about 500 to 1000 angstroms.

Furthermore, it is preferred that the porous particles have a porosity in the range of about 10 to 75%. Porosity of less than about 10% presents difficulty in obtaining a specific surface area sufficient to ensure the desired adsorption, and porosity above about 75% means a reduction in the strength of the resulting particles. And, since satisfactory effects can be obtained at the porosity of about 75% or less, it is not necessary to increase beyond about 75%.

The porous particles of the calcium phosphate compound can be produced by using any conventional methods. For example, they can be produced from starting particles which are crystalline particles of a calcium phosphate compound synthesized in a well-known wet process. A slurry—preferably a slurry in water—of the starting particles is directly spray-dried to form secondary particles, or spray dried after addition of an additive such as a viscosity modifier, particles or fibers of an organic compound which are capable of being dissipated upon heating the slurry.

The resulting secondary particles are porous particles by themselves, and accordingly they may be used as a starting material without further treatment. And, if it is desired to obtain porous particles or granules of the calcium phosphate compound having a highly increased porosity, such porous granules can be produced by the following method. Namely, the secondary particles are again suspended to prepare a slurry—preferably a slurry in water—of the secondary particles, followed by molding the slurry in a wet process or the secondary particles are molded in a dry process under the pressure to produce a block body of the calcium phosphate compound. In the preparation of the slurry, any organic compound which may be dissipated from the block body during the subsequent calcination process may be added to the slurry in order to assist the formation of the pores in the resulting granules. However, such addition of the organic compound may be omitted, because in the absence of such organic compound, a pore size or diameter of the resulting porous granules can be controlled by changing the calcination temperature and other conditions.

The obtained block body is then calcined at a temperature ranging from about 500° C. to 1300° C. A calcination temperature of less than about 500° C. is insufficient to complete thermal dissipation of the organic compound and calcination of the block body. And, if the calcination of the block body is carried out at an elevated temperature above about 1300° C., an excessively densified calcined body may be produced or an undesired decomposition of the calcium phosphate may be caused. The calcined block body is pulverized and then classified or sieved to obtain porous granules having a desired particle diameter. The pore size of the resulting porous granules can be controlled by suitably varying the size of the crystalline particles of the calcium phosphate compound in the starting slurry used in the preparation of the secondary particles, the viscosity of the slurry, additives and others.

Similarly, the spherical particles having a surface portion comprising or consisting of, or consisting essentially or substantially of the calcium phosphate compound can be produced in accordance with a variety of well-known methods. For example, they can be produced by using a method which comprises mixing spherical inorganic or organic particles with powders of the calcium phosphate compound, followed by compressing the mixture, to thereby coat the surface of the spherical particles with the calcium phosphate powders, a method which comprises physically impinging particles of the calcium phosphate compound against polymeric particles to thereby coat the surface of the polymeric particles with the calcium phosphate compound as a result of partial penetration of said calcium phosphate particles into said polymeric particles, or other conventional methods.

In the above-mentioned production of the spherical particles having a surface coated with the calcium phosphate compound, the inorganic particles used as a core in the first methods include a variety of spherical particles of inorganic substances such as silica, alumina, titania, magnesium carbonate and the like, and the organic particles include a variety of thermoplastic resins or thermosetting resins. Typical examples of thermoplastic resins include nylon, polyethylene, polypropylene, polystyrene, acrylic resins, thermoplastic polyurethane and the like. Typical examples of the thermosetting resins include phenolic resins, epoxy resins, melamine resins, urea resins, unsaturated polyester, alkyd resin, thermosetting polyurethane, ebonite and the like.

The spherical particles having a surface portion of the calcium phosphate compound used in the practice of the present invention preferably have a layer of the calcium phosphate compound with a thickness in the range of about 0.1 to 5.0 microns as a surface layer thereof. A layer thickness of less than about 0.1 microns does not ensure satisfactory adsorption, and even if the layer thickness is increased to above about 5.0 microns, a corresponding increase in adsorptivity cannot be attained.

The forms of the washing agents according to the present invention are not restricted to the specific forms, and accordingly they may include, for example, a liquid form, an emulsified cream form, a gel form, a solid form and the like. If it is desired to retain a stable dispersion state in the washing agents, the cream form, gel form or solid form will be more preferable than the liquid form.

Generally, conventional washing agents contain as principal components thereof alkaline soaps and/or different types of surface active agents, and further contain many additives such as a moisture-retaining agent, a foam-increasing agent, a germicide or bactericide, a preservative, a coloring agent, a perfume, a pearling agent, an emulsifying agent, a conditioning agent, a thickening agent and others. In the practice of the present invention, these conventional additives and components may be advantageously applied to the preparation of the washing agents.

Alkaline soaps include both the sodium soaps and the potassium soaps, typical examples of which soaps include sodium or potassium salts of fatty acids such as stearic acid, palmitic acid, myristic acid, lauric acid and the like. These soaps may be used alone or in combinations of two or more soaps.

In the washing agents of the present invention, a surface active agent may be used as a washing component in place of or in combination with the alkaline soaps. The surface active agents used herein are not restricted to specific ones, and accordingly they can be freely selected from a wide variety of well-known surface active agents. Typical examples of useful surface active agents include amphoteric surface active agents such as 2-alkyl-N-carboxymethyl-N-hydroxyethylimidazolinium betaine, alkyldiethylene triaminoacetic acid and the like, nonionic surface active agents such as coconut oil fatty acid diethanolamide, polyoxyethylene cetyl ether, polyoxylanolinether, polyoxyethylenecholesterol and the like, anionic surface active agents such as sodium α-olefinsulfonate, sodium alkylbenzenesulfonate and the like, and cationic surface active agents such as alkyltrimethylammonium halide and the like. These surface active agents may be used alone or in combinations of two or more agents.

The moisture-retaining agents used herein include, for example, higher alcohols such as glycerin, propylene glycol, cetyl alcohol and the like. These agents may be used alone or in mixtures of two or more agents.

The foam-increasing agents or foaming agents include, for example, alkyl salts of sulfuric acid, oxides and the like.

Further, in order to increase the capability of removing germs and bacteria, a germicide or bactericide may be added to the washing agents. Typical examples of useful germicides and bactericides include quaternary ammonium salts such as trichlorohydroxydiphenyl ether, benzylcetyl dimethylammonium chloride, benzalkonium chloride, benzethonium chloride and the like.

The preservatives include, for example, alkylpyridinium salts, a benzoic acid, alkylesters of paraoxybenzoic acid and the like.

Pearling or pearl agents include generally used ethylene glycols of distearic acid and the like.

Furthermore, the emulsifying agents include, for example, glycolesters of fatty acids and the like, the conditioning agents include, for example, glycerides and the like, and the thickening agents include, for example, polyvinyl alcohols and the like.

In addition to these additives, if desired, squalane may be added as an oily raw material, and chamomile oil, glycyrrhetinic acid salts and the like may be added as an antiphlogistic to the washing agents.

In the preparation of the washing agents according to the present invention, if liquid, creamy or gel-like products are desired to be prepared, such products can be prepared, for example, by dissolving water-soluble components in a purified water, and thoroughly mixing the solution with other components by stirring and, if desired, by heating. The resulting mixture is cooled by stirring, and further stirred after addition of a perfume. When solid soaps are desired to be produced, a soap base produced in the conventional methods can be added with the necessary components such as two types of hydroxyapatite particles having different particle diameters, perfume and others, followed by subjecting the mixture to the conventional processes for the production of framed soaps or milled soaps.

The present invention will be further described with reference to working examples thereof. Note, however, that the present invention should not be restricted to these examples.

EXAMPLE 1

Preparation of Creamy Washing Agent

A washing agent having the following formulation was prepared.

| component | amount |
| --- | --- |
| spherical hydroxyapatite particles (average particle diameter: 31 μm) | 1.8% by wt. |
| spherical hydroxyapatite particles (average particle diameter: 105 μm) | 0.2% by wt. |
| trichlorohydroxydiphenyl ether | 2.0% by wt. |
| stearic acid | 10.0% by wt. |
| palmitic acid | 8.0% by wt. |
| myristic acid | 12.0% by wt. |
| lauric acid | 5.0% by wt. |
| squalane | 1.0% by wt. |
| cetyl alcohol | 2.0% by wt. |
| glycerin | 18.5% by wt. |
| propylene glycol | 3.0% by wt. |
| potassium hydroxide | 5.0% by wt. |
| coloring agent, perfume and preservative | trace amount |
| purified water | balance |

The water-soluble components, i.e., glycerin, propylene glycol and potassium hydroxide were dissolved in a purified water. On the other hand, other components exclusive of a perfume were mixed and retained at a temperature in the range of about 60 to 70° C., and then the mixture was gradually added to the previously prepared aqueous solution of the water-soluble components by stirring. After the addition of the mixture was completed, the temperature in the range of about 60 to 70° C. was maintained by stirring for some time. Then, the mixture was cooled by stirring, and the cooled mixture was further cooled by stirring, after addition of the perfume. The product of the washing agent was thus obtained.

EXAMPLE 2

Preparation of Solid Soap

A solid soap having the following formulation was prepared by mixing a soap base consisting of the beef tallow- and coconut oil fatty acid-originated soap with other components, followed by sufficient milling to produce the solid soap.

| component | amount |
| --- | --- |
| spherical hydroxyapatite particles (average particle diameter: 16 μm) | 0.7% by wt. |
| spherical hydroxyapatite particles (average particle diameter: 88 μm) | 0.3% by wt. |
| soap base consisting of the beef tallow- and coconut oil fatty acid-originated soap | 90.0% by wt. |
| coloring agent, perfume and preservative | trace amount |
| purified water | balance |

EXAMPLE 3

Preparation of Creamy Washing Agent

A creamy washing agent having the following formulation was prepared in a manner similar to that of Example 1.

| component | amount |
| --- | --- |
| spherical hydroxyapatite particles (average particle diameter: 30 μm) | 1.0% by wt. |
| spherical hydroxyapatite particles (average particle diameter: 121 μm) | 0.8% by wt. |
| trichlorohydroxydiphenyl ether | 1.0% by wt. |
| stearic acid | 11.0% by wt. |
| paimitic acid | 8.0% by wt. |
| myristic acid | 12.0% by wt. |
| lauric acid | 5.0% by wt. |
| squalane | 1.0% by wt. |
| cetyl alcohol | 2.0% by wt. |
| glycerin | 18.5% by wt. |
| propylene glycol | 3.0% by wt. |
| sodium hydroxide | 6.2% by wt. |
| coloring agent, perfume and preservative | trace amount |
| purified water | balance |

I claim:

1. A washing agent which comprises spherical particles having an average particle diameter in the range of about 2 to 40 microns, at least a surface portion of which particles comprises a calcium phosphate compound having a Ca/P ratio in the range of about 1.0 to 2.0, and spherical particles having an average particle diameter in the range of about 80 to 200 microns, at least a surface portion of which particles comprises a calcium phosphate compound having a Ca/P ratio of about 1.0 to 2.0.

2. A washing agent according to claim 1 in which said spherical particles having an average particle diameter in the range of about 2 to 40 microns and said spherical particles having an average particle diameter in the range of about 80 to 200 microns are contained in a ratio by weight in the range of about 50:50 to 99.9:0.1.

3. A washing agent according to claim 1 in which a total amount of said spherical particles, at least a surface portion of which particles comprises calcium phosphate compound having a Ca/P ratio in the range of about 1.0 to 2.0, is about 0.01 to 10% by weight.

4. A washing agent according to claim 2 in which a total amount of said spherical particles, at least a surface portion of which particles comprises calcium phosphate compound having a Ca/P ratio in the range of about 1.0 to 2.0, is about 0.01 to 10% by weight.

5. The washing agent according to claim 1 in which a total amount of said spherical particles, at least a surface portion of which particles comprises a calcium phosphate compound having a Ca/P ratio in the range of about 1.0 to 2.0, is about 0.1 to 5% by weight.

6. The washing agent according to claim 1 in which the calcium phosphate compound having a Ca/P ratio in the range of about 1.0 to 2.0 comprises at least one member selected from the group consisting of hydroxyapatite, fluorapatite, tricalcium phosphate, tetrabasic calcium phosphate, $Ca_{10}(PO_4)_6(OH)_2$, $Ca_{10}(PO_4)_6F_2$, $Ca_{10}(PO_4)_6Cl_2$, $Ca_3(PO_4)_2$, $Ca_2P_2O_7$, $Ca_4O(PO_4)_2$, and $CaHPO_4$.

7. The washing agent according to claim 6 in which the calcium phosphate compound having a Ca/P ratio in the range of about 1.0 to 2.0 comprises hydroxyapatite.

8. The washing agent according to claim 1 in which the spherical particles comprise particles of the calcium phosphate compound having a Ca/P ratio in the range of about 1.0 to 2.0.

9. The washing agent according to claim 8 in which the spherical particles comprise porous particles comprising agglomerated primary particles having a specific surface area of at least about 10 m$^2$/g and a pore size of about 500 to 1000 angstroms.

10. The washing agent according to claim 8 in which the spherical particles comprise porous particles having a porosity of about 10 to 75%.

11. The washing agent according to claim 1 in which the spherical particles comprise at least one member selected from the group consisting of spherical inorganic and organic particles, having surfaces coated with the calcium phosphate compound having a Ca/P ratio in the range of about 1.0 to 2.0.

12. The washing agent according to claim 11 in which the calcium phosphate compound having a Ca/P ratio in the range of about 1.0 to 2.0 comprises a layer with a thickness of about 0.1 to 5.0 microns.

13. The washing agent according to claim 11 in which the spherical particles comprise at least one member selected from the group consisting of silica, alumina, titania, and magnesium carbonate particles, having surfaces coated with the calcium phosphate compound having a Ca/P ratio in the range of about 1.0 to 2.0.

14. The washing agent according to claim 11 in which the spherical particles comprise polymeric particles, having surfaces coated with the calcium phosphate compound having a Ca/P ratio in the range of about 1.0 to 2.0.

15. The washing agent according to claim 14 in which the polymeric particles have surfaces partially penetrated by particles of the calcium phosphate compound having a Ca/P ratio in the range of about 1.0 to 2.0.

16. The washing agent according to claim 1 further comprising at least one member selected from the group consisting of alkaline soaps.

17. The washing agent according to claim 1 further comprising at least one member selected from the group consisting of surface active agents.

18. A washing agent which comprises spherical particles having an average particle diameter in the range of about 10 to 35 microns, at least a surface portion of which particles comprises a calcium phosphate compound having a Ca/P ratio in the range of about 1.0 to 2.0, and spherical particles having an average particle diameter in the range of about 80 to 200 microns, at least a surface portion of which particles comprises a calcium phosphate compound having a Ca/P ratio in the range of about 1.0 to 2.0.

19. A washing agent which comprises first spherical particles having an average particle diameter in the range of about 2 to 40 microns, at least a surface portion of which particles comprises a calcium phosphate compound having a Ca/P ratio in the range of about 1.0 to 2.0, and second spherical particles having an average particle diameter in the range of about 85 to 130 microns, at least a surface portion of which particles comprises a calcium phosphate compound having a Ca/P ratio in the range of about 1.0 to 2.0.

20. The washing agent according to claim 19 in which the first spherical particles have an average particle diameter in the range of about 10 to 35 microns.

* * * * *